United States Patent [19]

Houlihan

[11] 3,953,600

[45] Apr. 27, 1976

[54] CITRONELLYL BENZIMIDAZOLES

[75] Inventor: William J. Houlihan, Mountain Lakes, N.J.

[73] Assignee: Sandoz, Inc., E. Hanover, N.J.

[22] Filed: Aug. 21, 1975

[21] Appl. No.: 606,364

Related U.S. Application Data

[63] Continuation-in-part of Ser. No. 534,684, Dec. 20, 1974, abandoned.

[52] U.S. Cl. ............................. 424/273; 260/307.2
[51] Int. Cl.$^2$ .................................... C07D 235/18
[58] Field of Search ................... 260/309.2; 424/273

[56] References Cited

UNITED STATES PATENTS

| | | | |
|---|---|---|---|
| 3,080,282 | 3/1963 | Shunk | 260/309.2 |
| 3,162,574 | 12/1964 | Forsyth | 260/309.2 |
| 3,192,227 | 6/1965 | Brown et al. | 260/309.2 |

OTHER PUBLICATIONS

Makoto et al., Chem. Abst., 1972, Vol. 77, No. 165289d.

*Primary Examiner*—Natalie Trousof
*Attorney, Agent, or Firm*—Gerald D. Sharkin; Robert S. Honor; Thomas O. McGovern

[57] ABSTRACT

Citronellyl benzimidazoles, e.g., (±) 1-(3,7-dimethyl-6-octen-1-yl)-2-phenylbenzimidazole, are prepared by reacting an alkali metal salt of a 2-phenylbenzimidazole with citronellyl halide and are useful as hypolipidemic agents.

13 Claims, No Drawings

CITRONELLYL BENZIMIDAZOLES

This application is a continuation-in-part of copending application Ser. No. 534,684, filed Dec. 20, 1974, now abandoned.

This invention relates to citronellyl benzimidazoles. More particularly, it relates to (±) 1-(3,7-dimethyl-6-octen-1-yl)-2-substituted or unsubstituted phenylbenzimidazoles, to processes for their preparation, and pharmaceutically acceptable acid addition salts thereof.

The compounds of this invention may be represented by the following structural formula:

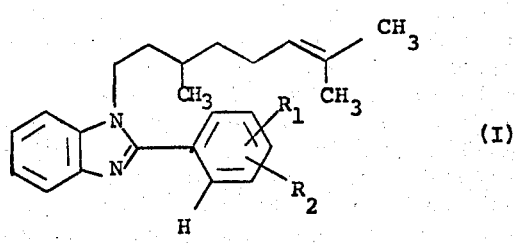

(I)

where
$R_1$ and $R_2$ each independently represent hydrogen, halo having an atomic weight of about 19 to 36, lower alkyl, i.e., alkyl having 1 to 4 carbon atoms, e.g., methyl, ethyl, isopropyl, and the like, lower alkoxy, i.e., alkoxy having 1 to 4 carbon atoms, e.g., methoxy, ethoxy, isopropoxy and the like, trifluoromethyl, or
$R_1$ and $R_2$ on adjacent carbon atoms together represent methylenedioxy, provided that when $R_1$ and $R_2$ are both trifluoromethyl or t-butyl, or when one of $R_1$ and $R_2$ is trifluoromethyl and the other t-butyl, they are on other than adjacent carbon atoms.

The compounds of formula (I) may be prepared according to the following reaction scheme:

where
X represents chlorine or bromine, and
M represents an alkali metal, e.g., sodium, potassium and the like, and
$R_1$, $R_2$ and the proviso are as defined above.

The compounds of formula (I) are prepared by treating a compound of the formula (II) with a compound of the formula (III) in the presence of an inert atmosphere, e.g., nitrogen, helium or Argon, preferably nitrogen, and in the presence of an inert organic solvent. Although the particular solvent employed is not critical, the preferred solvents include the aromatic hydrocarbons such as benzene, toluene and the like, the ethers such as diethylether, tetrahydrofuran and the like, or dimethylformamide, preferably tetrahydrofuran. The temperature of the reaction is not critical, but it is preferred that the reaction be run from about 10° to 80°C., preferably from about 20° to 30°C. The reaction is run from about 10 to 50 hours, preferably from about 15 to 24 hours. The resulting product is recovered using conventional techniques, e.g., column chromatography.

The compounds of formula (II) are prepared according to the following reaction scheme:

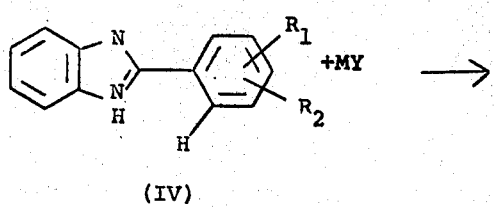

(IV)

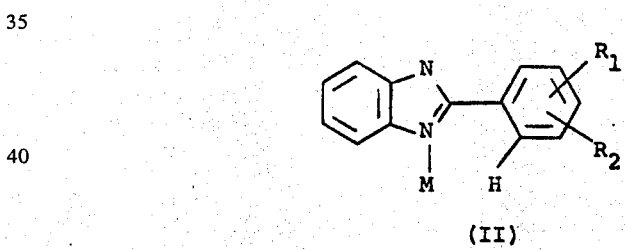

(II)

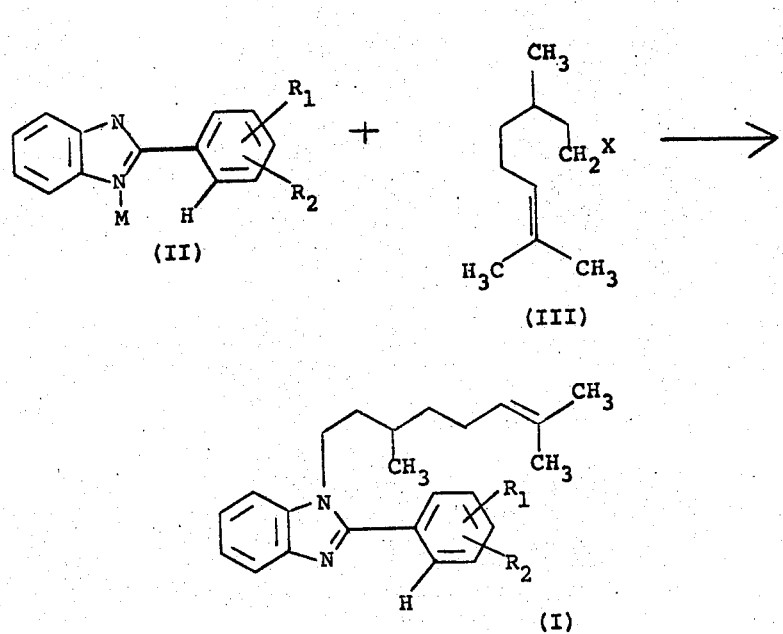

where
MY represents an alkali metal hydride, e.g., sodium hydride or potassium hydride, and M, $R_1$, $R_2$ and the proviso are as defined above.

The compounds of formula (II) are prepared by reacting a compound of the formula (IV) with an alkali metal hydride, such as sodium hydride, potassium hydride, or lithium hydride, preferably sodium hydride, in the presence of an inert atmosphere, e.g., nitrogen, helium or argon and in the presence of an inert organic solvent. Although the particular solvent employed is not critical, the preferred solvents include the aromatic hydrocarbons such as benzene, toluene and the like, the ethers such as diethylether, tetrahydrofuran and the like, or dimethylformamide, preferably tetrahydrofuran. The temperature of the reaction is not critical, but it is preferred that the reaction be run from about 20° to 75°C., preferably from about 40° to 60°C. The reaction is run from about 1 to 10 hours, preferably from about 2 to 4 hours.

Certain of the compounds of formulae (II), (III), and (IV) are known and may be prepared by methods described in the literature. Those compounds of formulae (II), (III), and (IV) not specifically disclosed may be prepared by analogous methods from known starting materials.

It will be understood that the compounds of formula (I) may exist in the form of optically active isomers, which can be separated and recovered by conventional techniques, and such isomeric forms are included within the scope of this invention. For example (+) 1-(3,7-dimethyl-6-octen-1-yl)-2-phenylbenzimidazole and (−) 1-(3,7-dimethyl-6-octen-1-yl)-2-phenylbenzimidazole.

The compounds of formula (I) are useful because they possess pharmacological activity in animals. In particular, the compounds are useful as hypolipidemic agents in the treatment of lipidemia as indicated by the fall in cholesterol and/or triglyceride levels in male albino Wistar rats weighing 110–130 g. initially. The rats are maintained on drug-free laboratory chow diet for 7 days and then divided into groups of 6 to 10 animals. Each group, with the exception of the control, is then given orally 7.5 to 500 milligrams per kilogram of body weight per diem of the test compound for 6 days. At the end of this period, the animals are anesthetized with sodium hexobarbital and bled from the carotid arteries. Serum or plasma samples are collected and 1.0 ml. of the serum is added to 9.0 ml. redistilled isopropanol. Two autoanalyzer cupsful of a mixture of zeolite-copper hydroxide and Lloydds reagent (Kessler, G., and Lederer, H., 1965, Technicon Symposium Mediad Inc., New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

When the compounds are employed for the above utility, they may be combined with one or more pharmaceutically acceptable carriers or adjuvants and may be administered orally in such forms as tablets, capsules, dispersible powders, granules, syrups, elixirs, suspensions, and the like, or parenterally in the form of sterile injectable solutions or suspensions. These pharmaceutical preparations may contain up to about 90% of the active ingredient in combination with the carrier or adjuvant. Furthermore, the compounds of formula (I) may be similarly administered in the form of their non-toxic, pharmaceutically acceptable acid addition salts. Such salts possess the same order of activity as the free base, are readily prepared by reacting the base with an appropriate acid, and, accordingly, are included within the scope of the invention. Representative of the acid addition salts are the neutral acid salts such as the hydrochloride, hydrobromide sulfate, phosphate and the like, and the organic salts such as succinate, benzoate, acetate, and the like.

The hypolipidemic effective dosage of active ingredient employed for the treatment of lipidemia may vary depending on the particular compound employed, the mode of administration and the severity of the condition being treated. However, in general, satisfactory results are obtained when the compounds of formula (I) are administered at a daily dosage of from about 4 milligrams to about 250 milligrams per kilogram of animal body weight, preferably given in divided doses two to four times a day, or in sustained release form. For most large mammals, the total daily dosage is from about 300 to about 3000 milligrams. Dosage forms suitable for internal use comprise from about 75 to 1500 milligrams of the active compound in intimate admixture with a solid or liquid pharmaceutically acceptable carrier or diluent.

A representative formulation suitable for oral administration is a capsule prepared by standard encapsulating techniques which contain the following and may be administered 2 to 4 times a day in the treatment of lipidemia.

| Ingredient | Weight (mg.) |
|---|---|
| (±) 1-(3,7-dimethyl-6-octen-1-yl)-2-phenylbenzimidazole | 150 |
| Inert filler (starch, lactose, kaolin, etc.) | 300 |

EXAMPLE 1

(±) 1-(3,7-dimethyl-6-octen-1-yl)-2-phenylbenzimidazole

In a flask equipped with a stirrer, condenser and nitrogen inlet tube, there is added 90 ml. of anhydrous tetrahydrofuran, 30 ml. of anhydrous dimethylformamide and 9.7 g. (0.05 mole) of 2-phenylbenzimidazole. The resulting system is then blanketed with nitrogen, stirring is initiated and 2.2 g. (0.053 mole) of 57% sodium hydride mineral oil dispersion is added in one portion. The mixture is then heated to 50° for about 2 hours. After cooling to room temperature, a solution of 12.0 g. (0.053 mole) of (±) 1-bromo-3,7-dimethyl-6-octene in 50 ml. of dry tetrahydrofuran is added dropwise. The resulting mixture is stirred overnight at room temperature and the resultant salts are removed by filtration. The filtrate is concentrated in vacuo. The resultant oil is dissolved in chloroform and chromatographed on silica gel using methylenechloride as the eluant to give (±)1-(3,7-dimethyl-6-octen-1-yl)-2-phenylbenzimidazole, NMR ($CDCl_3$) δ0.72–2.18 (16H, complex multiplet,

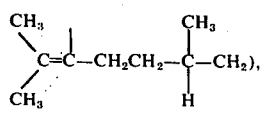

4.23 (2H, triplet, J=7cps, CH$_2$N), 5.00 (1H, triplet, J=7cps, HC=C), 7.13–7.95 (9H, multiplet, C$_6$H$_5$ and C$_6$H$_4$). Anal. Calcd. for C$_{23}$H$_{28}$N$_2$:C, 83.1; H, 8.5; N, 8.4. Found:C, 83.3; H, 8.8; N, 8.0.

Following the above procedure and using, in place of 2-phenylbenzimidazole, an equivalent amount of
- a. 2-(p-chlorophenyl)benzimidazole,
- b. 2-(p-tolyl)benzimidazole,
- c. 2-(p-anisyl)benzimidazole,
- d. 2-(p-trifluoromethylphenyl)benzimidazole,
- e. 2-(3,4-dichlorophenyl)benzimidazole,
- f. 2-(3,4-methylenedioxyphenyl)benzimidazole,
- g. 2-(m-tolyl)benzimidazole, or
- h. 2-(o-fluorophenyl)benzimidazole, there is obtained
- a. (±)1-(3,7-dimethyl-6-octen-1-yl)-2-(p-chlorophenyl)benzimidazole,
- b. (±)1-(3,7-dimethyl-6-octen-1-yl)-2-(p-tolyl)benzimidazole,
- c. (±)1-(3,7-dimethyl-6-octen-1-yl)-2-(p-anisyl)benzimidazole,
- d. (±)1-(3,7-dimethyl-6-octen-1-yl)-2-(p-trifluoromethylphenyl) benzimidazole,
- e. (±)1-(3,7-dimethyl-6-octen-1-yl)-2-(3,4-dichlorophenyl) benzimidazole,
- f. (±)1-(3,7-dimethyl-6-octen-1-yl)-2-(3,4-methylenedioxyphenyl)benzimidazole,
- g. (±)1-(3,7-dimethyl-6-octen-1-yl)-2-(m-tolyl)benzimidazole, or
- h. (±)1-(3,7-dimethyl-6-octen-1-yl)-2-(o-fluorophenyl)benzimidazole, respectively.

The (±)1-(3,7-dimethyl-6-octen-1-yl)-2-phenylimidazole of this example is an effective hypolipidemic agent when orally administered to an animal suffering from lipidemia at a dosage of 150 mg. four times per day.

What is claimed is:
1. A compound of the formula

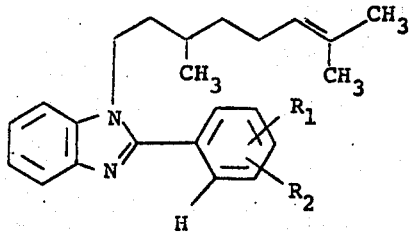

where
R$_1$ and R$_2$ each independently represent hydrogen, halo having an atomic weight of about 19 to 36, lower alkyl having 1 to 4 carbon atoms, lower alkoxy having 1 to 4 carbon atoms, trifluoromethyl, or
R$_1$ and R$_2$ on adjacent carbon atoms together represent methylenedioxy, provided that when R$_1$ and R$_2$ are both trifluoromethyl or t-butyl or when one of R$_1$ and R$_2$ is trifluoromethyl and the other is t-butyl they are on other than adjacent carbon atoms;

or a pharmaceutically acceptable acid addition salt thereof.

2. A compound of claim 1 in free base form.
3. A compound according to claim 1 in which both R$_1$ and R$_2$ are hydrogen.
4. The compound of claim 1 which is (±)1-(3,7-dimethyl-6-octen-1-yl)-2-phenylbenzimidazole.
5. The compound of claim 1 which is (±)1-(3,7-dimethyl-6-octen-1-yl)-2-(p-chlorophenyl)benzimidazole.
6. The compound of claim 1 which is (±)1-(3,7-dimethyl-6-octen-1-yl)-2-(p-tolyl)benzimidazole.
7. The compound of claim 1 which is (±)1-(3,7-dimethyl-6-octen-1-yl)-2-(p-anisyl)benzimidazole.
8. The compound of claim 1 which is (±)1-(3,7-dimethyl-6-octen-1-yl)-2-(p-trifluoromethylphenyl)-benzimidazole.
9. The compound of claim 1 which is (±)1-(3,7-dimethyl-6-octen-1-yl)-2-(3,4-dichlorophenyl)benzimidazole.
10. The compound of claim 1 which is (±)1-(3,7-dimethyl-6-octen-1-yl)-2-(m-tolyl)benzimidazole.
11. The compound of claim 1 which is (±)1-(3,7-dimethyl-6-octen-1-yl)-2-(o-fluorophenyl)benzimidazole.
12. A hypolipidemic composition comprising an effective amount of a compound of claim 1 and a pharmaceutically acceptable diluent or carrier therefor.
13. A method of treating lipidemia which comprises orally or parenterally administering to a mammal in need of said treatment a hypolipidemic effective amount of a compound of claim 1.

* * * * *